United States Patent
Englund et al.

(10) Patent No.: US 9,568,545 B2
(45) Date of Patent: Feb. 14, 2017

(54) SYSTEMS AND METHODS FOR PRECISION OPTICAL IMAGING OF ELECTRICAL CURRENTS AND TEMPERATURE IN INTEGRATED CIRCUITS

(71) Applicant: THE TRUSTEES OF COLUMBIA UNIVERSITY IN THE CITY OF NEW YORK, New York, NY (US)

(72) Inventors: Dirk R. Englund, New York, NY (US); Matthew E. Trusheim, Cambridge, MA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 240 days.

(21) Appl. No.: 14/566,059

(22) Filed: Dec. 10, 2014

(65) Prior Publication Data

US 2015/0137793 A1   May 21, 2015

Related U.S. Application Data

(63) Continuation of application No. PCT/US2013/045795, filed on Jun. 14, 2013.
(Continued)

(51) Int. Cl.
*G01R 31/00*  (2006.01)
*G01R 31/28*  (2006.01)
(Continued)

(52) U.S. Cl.
CPC ........... *G01R 31/2851* (2013.01); *G01K 11/00* (2013.01); *G01N 21/64* (2013.01);
(Continued)

(58) Field of Classification Search
CPC .. G01N 21/64; G01N 21/643; G01N 21/6421; G01N 21/6458; G01N 21/6486; G01N 21/6489; G01N 33/585; G01N 33/587; G01R 31/00; G01R 31/26
See application file for complete search history.

(56) References Cited

U.S. PATENT DOCUMENTS

2010/0308813 A1* 12/2010 Lukin ................. G01R 33/032
324/244.1
2010/0315079 A1   12/2010 Lukin et al.
(Continued)

FOREIGN PATENT DOCUMENTS

WO   WO 2012/034924   3/2012

OTHER PUBLICATIONS

August, et al., "Compressive hyperspectral imaging by random separable projections in both the spatial and the spectral domains", *Applied Optics*, vol. 52, No. 10 (Apr. 1, 2013).
(Continued)

*Primary Examiner* — Minh N Tang
(74) *Attorney, Agent, or Firm* — Baker Botts, LLP

(57) ABSTRACT

Systems and methods for precision optical imaging of electrical currents and temperature in integrated circuits are disclosed herein. In one aspect of the disclosed subject matter, a method for detecting a characteristic of an integrated circuit can include depositing at least one diamond structure, having at least one color center therein, onto a side of the integrated circuit.

21 Claims, 7 Drawing Sheets

---

601. Deposit at least one diamond structure, having at least one color center therein, onto a side of the integrated circuit

⬇

602. Apply an electromagnetic pump field to the at least one diamond structure

⬇

603. Monitor a spin state of the at least one color center by measuring an emission of photons from the at least one color center resulting from the electromagnetic pump field and an electromagnetic radiation of the integrated circuit

⬇

604. Detect detecting the characteristic of the integrated circuit based on a correlation between the emission of photons and the characteristic

Related U.S. Application Data

(60) Provisional application No. 61/662,666, filed on Jun. 21, 2012, provisional application No. 61/659,764, filed on Jun. 14, 2012.

(51) Int. Cl.
| | | |
|---|---|---|
| *G01K 11/00* | (2006.01) | |
| *G01R 31/311* | (2006.01) | |
| *G01N 21/64* | (2006.01) | |
| *G01R 19/00* | (2006.01) | |
| G01R 15/24 | (2006.01) | |
| G01R 23/17 | (2006.01) | |

(52) U.S. Cl.
CPC ........ *G01R 19/0092* (2013.01); *G01R 31/311* (2013.01); *G01N 2201/06113* (2013.01); *G01R 15/24* (2013.01); *G01R 23/17* (2013.01); *G01R 31/2884* (2013.01)

(56) References Cited

U.S. PATENT DOCUMENTS

| | | |
|---|---|---|
| 2011/0120890 A1 | 5/2011 | Macpherson et al. |
| 2011/0309265 A1 | 12/2011 | Babinec et al. |
| 2012/0019242 A1 | 1/2012 | Hollenberg et al. |

OTHER PUBLICATIONS

Maletinsky, et al., "A robust scanning diamond sensor for nanoscale imaging with single nitrogen-vacancy centres", *Nature Nanotechnology*, 7(5), Published Online Apr. 15, 2012 [retrieved Nov. 6, 2013]. Retrieved from ProQuest Technology Collection: http://dx.doi.org/10.1038/nnano.2012.50 p. 320-324.

International Search Report mailed Nov. 14, 2013 in PCT/US2013/045795.

\* cited by examiner

FIG. 6

601. Deposit at least one diamond structure, having at least one color center therein, onto a side of the integrated circuit

602. Apply an electromagnetic pump field to the at least one diamond structure

603. Monitor a spin state of the at least one color center by measuring an emission of photons from the at least one color center resulting from the electromagnetic pump field and an electromagnetic radiation of the integrated circuit

604. Detect detecting the characteristic of the integrated circuit based on a correlation between the emission of photons and the characteristic SYSTEMS AND METHODS FOR PRECISION OPTICAL IMAGING OF ELECTRICAL CURRENTS AND TEMPERATURE IN INTEGRATED CIRCUITS

CROSS REFERENCE TO RELATED APPLICATION

This application is a continuation of International Application No. PCT/US2013/045795, filed on Jun. 14, 2013, which claims priority from U.S. Provisional Application No. 61/662,666, filed on Jun. 21, 2012 and U.S. Provisional Application No. 61/659,764, filed on Jun. 14, 2012, which are each incorporated by reference herein in their entirety.

STATEMENT REGARDING FEDERALLY SPONSORED RESEARCH

This invention was made with government support under Grant No. FA9550-12-1-0045 awarded by the Air Force Office of Scientific Research, PECASE. The government has certain rights in the invention.

BACKGROUND

This disclosed subject matter relates to techniques for precision optical imaging of electrical currents and temperature in integrated circuits.

In certain instances, it can be desirable to image the temperature or the electric currents within an integrated circuit (IC). Certain thermal imaging techniques, such as liquid crystal thermography, Fluorescence microthermography, scanning thermal microscopy, infrared emission imaging, and thermoreflectance, can provide 400 nm of spatial resolution. Magnetic imaging techniques, which can employ magnetoresistance or anisotropic magnetoresistance (AMR) sensors, can be limited to micron-scale resolution (after software-based image reconstruction techniques), slow, and record at a limited number of sites simultaneously since they depend on moving/scanning sensors.

Accordingly, there exists a need for improved thermal and magnetic imaging techniques.

SUMMARY

Systems and methods for precision optical imaging of electrical currents and temperature in integrated circuits are disclosed herein.

In one aspect of the disclosed subject matter, methods for detecting a characteristic of an integrated circuit are provided. In one example, a method can include depositing at least one diamond structure, having at least one nitrogen vacancy (NV) color center therein, onto a side of the integrated circuit. An electromagnetic pump field can be applied to the NV center in the at least one diamond structure. The NV center can have a spin-triplet ground state with spin projections $m_s=0$, $-1$, and $+1$. In the absence of an external magnetic field, the energy of the sublevels $m_s=-1$, $+1$ can be equal. The frequency difference of the $m_s=+1$, $-1$ levels with respect to the $m_s=0$ level can be approximately equal to 2.87 GHz. The electron spin state of the NV color center can be initialized to $m_s=0$ by optical pumping since the NV center can decays through a spin-selective pathway. Subsequently, the spin state can be modified in the presence of an electromagnetic field produced by electrical currents in the integrated circuit, if the frequency of this electromagnetic field is close to the frequency difference between magnetic sublevels of the NV center. The modification can depend on the frequency, strength, and orientation of the electromagnetic field.

The NV spin state can then be recorded by measuring the emission of photons from it. The photon emission brightness can depend on the spin state and therefore can be used to infer the NV spin state. In this way, the optical initialization and readout of the NV spin state can be used to infer the strength, phase, and/or the orientation of the electromagnetic field originating from the integrated circuit. This information about the electromagnetic radiation can be used to infer the currents flowing in the integrated circuit. Characteristics of the integrated circuit can be detected based on a correlation between the emission of photons and the given characteristic. In some embodiments, the characteristic can be one of a current or a temperature. For example, a temperature in the integrated circuit can be measured, using a spin-protocol sensitive to temperature and insensitive to magnetic field.

The protocol can be pulsed or continuous-wave. For example, the protocol can be the pulsed technique disclosed in commonly assigned International Application No. PCT/US2012/055555, which is hereby incorporated by reference in its entirety. In the continuous wave case, a shift in the magnetic sublevel transition frequency can be monitored, and the shift can occur because of a dependence of the level splitting with temperature of approximately 73 kHz/degree Celsius. Both temperature and currents can be measured with a spatial resolution below the optical diffraction limit, using super-resolution imaging techniques such as Deterministic Emitter Switch Microscopy (DESM).

In some embodiments, a direct current magnetic field can be applied to the at least one color center. In some such embodiments, the characteristic can be a current, and the direct-current magnetic field can be swept to shift the NV magnetic sublevel transitions in frequency by the Zeeman effect. Thus, the NV's optically detected response to electromagnetic radiation from the integrated circuit can sweep across a spectrum and map out the spectrum of the electromagnetic radiation in the circuit.

In some embodiments, the color center can be a nitrogen vacancy (NV) center. Positive, ground, and negative spin states of the NV center can be monitored.

In some embodiments, the characteristic can be a current modulated with low amplitude, e.g., 1-10% of the operational current of the device, at a frequency as high as 10 MHz and as low as an inverse of an electron spin phase coherence time of the color center.

In some embodiments, a clock frequency of the integrated circuit can be modulated to sweep the frequency across the NV magnetic sublevel transition frequency. For example, the NV magnetic sublevel can be maintained at a particular splitting near 2.87 GHz, while the chip's clock frequency can be swept across it. Electromagnetic fields and currents in the integrated circuit can be measured at frequencies from 100 MHz to 10 GHz.

In some embodiments, an internal dipole of the color center can be calibrated. In some such embodiments, a full vector nature of a magnetic field resulting from the characteristic can be determined based on a predetermined correlation between the emission of photons, the internal dipole, and the magnetic field. The characteristic for each layer of a plurality of layers within the integrated circuit can be detected based on a predetermined correlation between the magnetic field and the characteristic.

In some embodiments, the diamond structure can be a plurality of nanodiamonds, which can be dissolved in a solvent and deposited onto a side of the integrated circuit by one of drop-casting, spin-coating, or atomizing.

In another aspect of the disclosed subject matter, systems for detecting a characteristic of an integrated circuit are provided. In an exemplary embodiment, a system can include a receptacle adapted to receive the integrated circuit. At least one diamond structure, having at least one NV color center, can be disposed on a side of the integrated circuit. An electromagnetic pump field source can pump the NV center (s) in the diamond structure. A monitoring device can monitor the electronic spin state of the at least one color center by measuring an emission of photons from the color center resulting from the electromagnetic pump field and an electromagnetic radiation of the integrated circuit to thereby detect the characteristic of the integrated circuit based on a correlation between the emission of photons and the characteristic. In some embodiments, the diamond structure can be a nanodiamond or a bulk diamond crystal. In some embodiments, the characteristic can be current or a temperature.

In some embodiments, a direct current magnetic field source can be coupled to the receptacle and adapted to apply a direct current magnetic field to the at least one color center. In some such embodiments, the direct current magnetic field source can sweep the direct current magnetic field to shift a magnetic sublevel of the at least one color center by the Zeeman effect.

In some embodiments, the color center can be a nitrogen vacancy (NV) center, and the monitoring device can be adapted to monitor the $m_s=+1$ spin state of the NV center, the $m_s=0$ spin state of the NV center, and a the $m_s=-1$ spin state of the NV center.

In some embodiments, the characteristic can be a current, which can be modulated with a small amplitude (1-10% of the normal operating current) at a frequency corresponding to an inverse of an electron spin phase coherence time of the color center.

In some embodiments, the characteristic can be a current, and the integrated circuit can have a modulated clock frequency which is swept across the NV's magnetic sublevel transition, which can be maintained to be constant in the presence of a fixed stationary magnetic field.

In some embodiments, the color center can include a calibrated internal dipole, and the monitoring device can detect the characteristic for each layer within the integrated circuit based on a predetermined correlation between the emission of photons, the internal dipole, the magnetic field, and the characteristic.

In some embodiments, the color center can be externally addressed with resonant microwave radiation with a known variable phase and the characteristic can be full phase information of the electromagnetic field of the integrated circuit.

The accompanying drawings, which are incorporated and constitute part of this disclosure, illustrate and serve to explain the principles of the disclosed subject matter.

BRIEF DESCRIPTION OF THE DRAWINGS

FIG. 6 is a flowchart illustrating a method for detecting a characteristic of an integrated circuit, in accordance with some exemplary embodiments of the disclosed subject matter.

Figure 1:
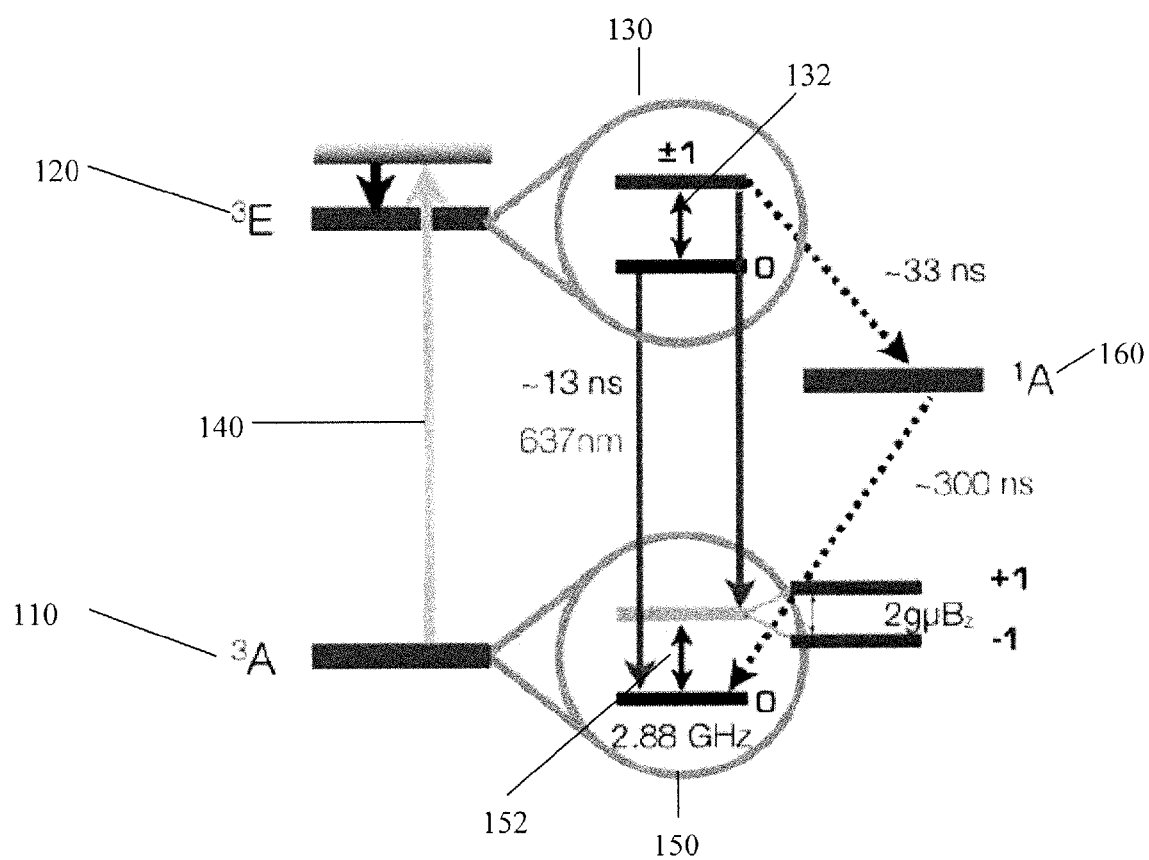
FIG. 1 is a diagram showing a nitrogen-vacancy (NV) center in diamond, in accordance with some exemplary embodiments of the disclosed subject matter.

Throughout the drawings, similar reference numerals and characters, unless otherwise stated, are used to denote like features, elements, components or portions of the illustrated embodiments. Moreover, while the disclosed subject matter will now be described in detail with reference to the FIGS., it is done so in connection with the illustrative embodiments.

DETAILED DESCRIPTION

Techniques for precision optical imaging of electrical currents and temperature in integrated circuits are presented.

Diamond nitrogen vacancy (NV) color centers can be formed when a substitutional nitrogen and a vacancy are created in the carbon lattice, replacing two carbons. Diamond NV centers can occur naturally or can be implanted in a diamond structure via ion radiation or the like. NV centers can exist in multiple radiative states, sometimes referred to as charge states, including a positively charged radiative state (NV+), a neutrally charged radiative state (NV0), and a negatively charged radiative state (NV−). The NV− center has an additional electron associated with it, creating a desirable electronic S=1 structure that has a long-lived spin triplet in its ground state that can be probed using optical and microwave excitation. The NV electron spin can act as a sensitive probe of the local environment, and its optical accessibility can allow its use in optically-detected magnetic resonance schemes. The electron spin state of an NV center can respond to the magnetic field created by currents or temperatures within an integrated circuit (IC).

Referring to FIG. 1 an exemplary NV center is illustrated. NV centers can absorb photons 140 with a wavelength around 532 nm and undergo photoluminescence (PL), which can be between 637 and 800 nm. A spin-dependent intersystem crossing 160 between excited state 120 triplet (3) to a metastable, dark singlet level 110 (S) can change the integrated PL for the spin states $|0\rangle$ and $|\pm 1\rangle$. The deshelving from the singlet 110 occurs primarily to the $|0\rangle$ spin state, which can provide a means to polarize the NV center.

As depicted in FIG. 1, transitions from the NV ground state 110 to the excited state 120 are spin-conserving, keeping $m_s$ constant. Such an excitation can be performed using laser light 140 at approximately 532 nm; however, other wavelengths can be used, such as blue (480 nm) and yellow (580 nm). While the electronic excitation pathway preserves spin, the relaxation pathways contain non-conserving transitions involving an intersystem crossing (or singlet levels).

In accordance with the disclosed subject matter, the NV centers can be used, for example, for magnetic field, current, or temperature imaging. Spin states in the diamond can enable magnetic field sensing on the nanometer scale with high precision. The magnetic field image can be used to reconstruct the currents that give rise to the magnetic fields. Furthermore, the NV centers can be uniquely identified by transitions between their magnetic sublevels, a property that can enable sub-optical spatial resolution. For example, single NV centers can be deterministically switched to locate emitters below 30 nm resolution. Diamond nanoprobes with NV centers can also be photostable. For example, single NV centers can emit without a change in brightness for months or longer. Additionally diamond is chemically inert and has surfaces that can be suitable for functionalization. NV centers can emit in excess of $10^6$ photons per second per center, far brighter than certain other light emitters.

In accordance with one aspect of the disclosed subject matter, a diamond nanoparticle including at least one NV center can be deposited onto the surface of an IC, as discussed below.

Figure 2:
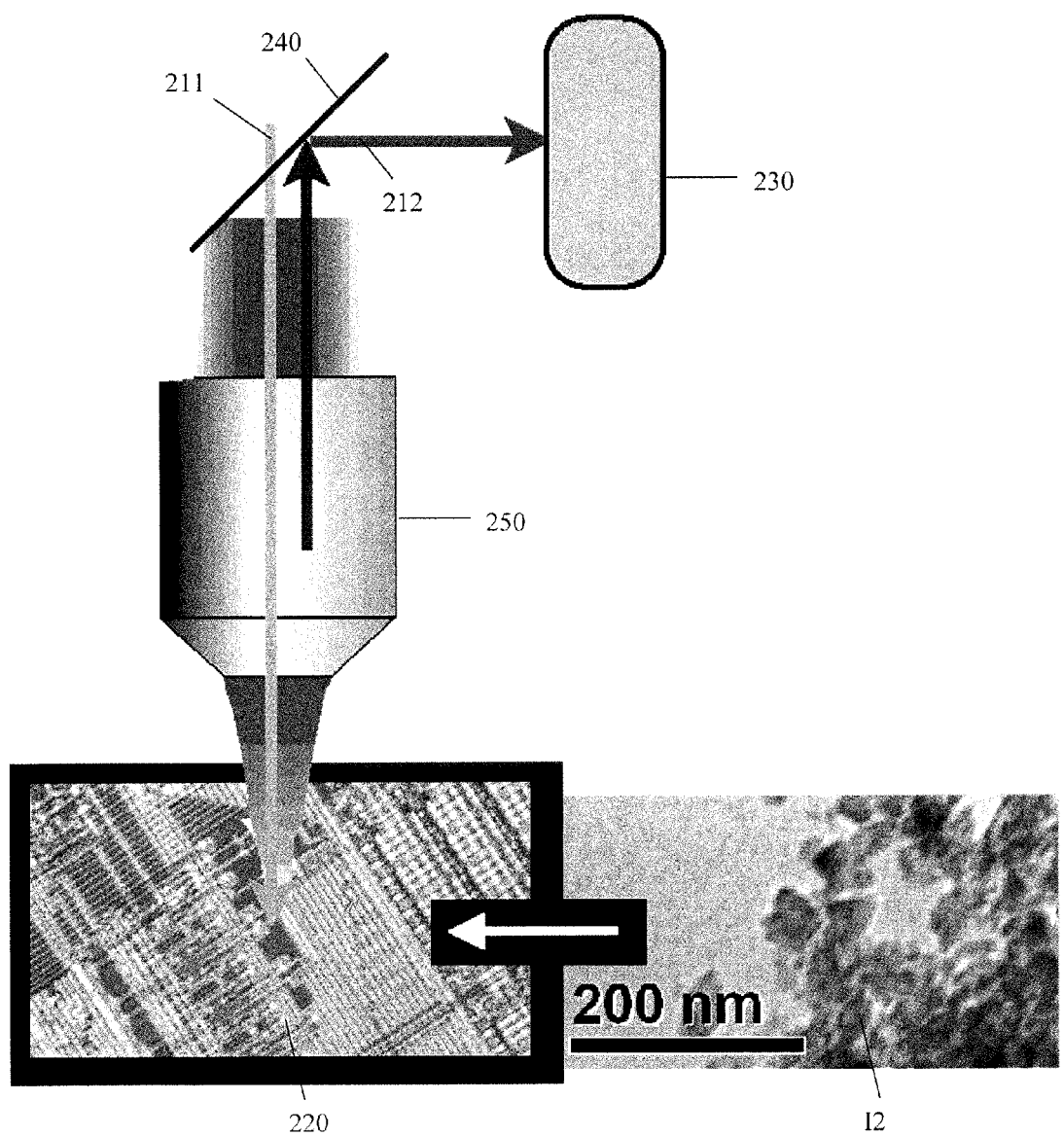
FIG. 2 is a diagram of nanodiamonds on an integrated circuit (IC) surface imaged in a microscope, in accordance with some exemplary embodiments of the disclosed subject matter.

Referring to FIG. 2, exemplary nanodiamonds on the surface of an IC are shown. A suitable light source (not pictured) can be used for optical pumping, as further described below. The pump light 211 can be directed through a dichromatic mirror 240 and an objective 250 to the surface of the IC 220. Photons in the pump light 211 can be absorbed by the NV centers within the nanodiamonds on the surface of the IC 220, thereby exciting the NV centers into an excited state. The NV centers can then transition back to the ground state, emitting fluorescent response 212, e.g., a photon with a wavelength between 637 and 800 nm. This fluorescent response can pass through the objective 250, and the dichromatic mirror 240 can direct the fluorescent response to a photodetector 230. The inset I2 shows an image of the nanodiamonds on the surface of the IC 220 obtained using a transmission electron microscope (TEM).

Figure 3:
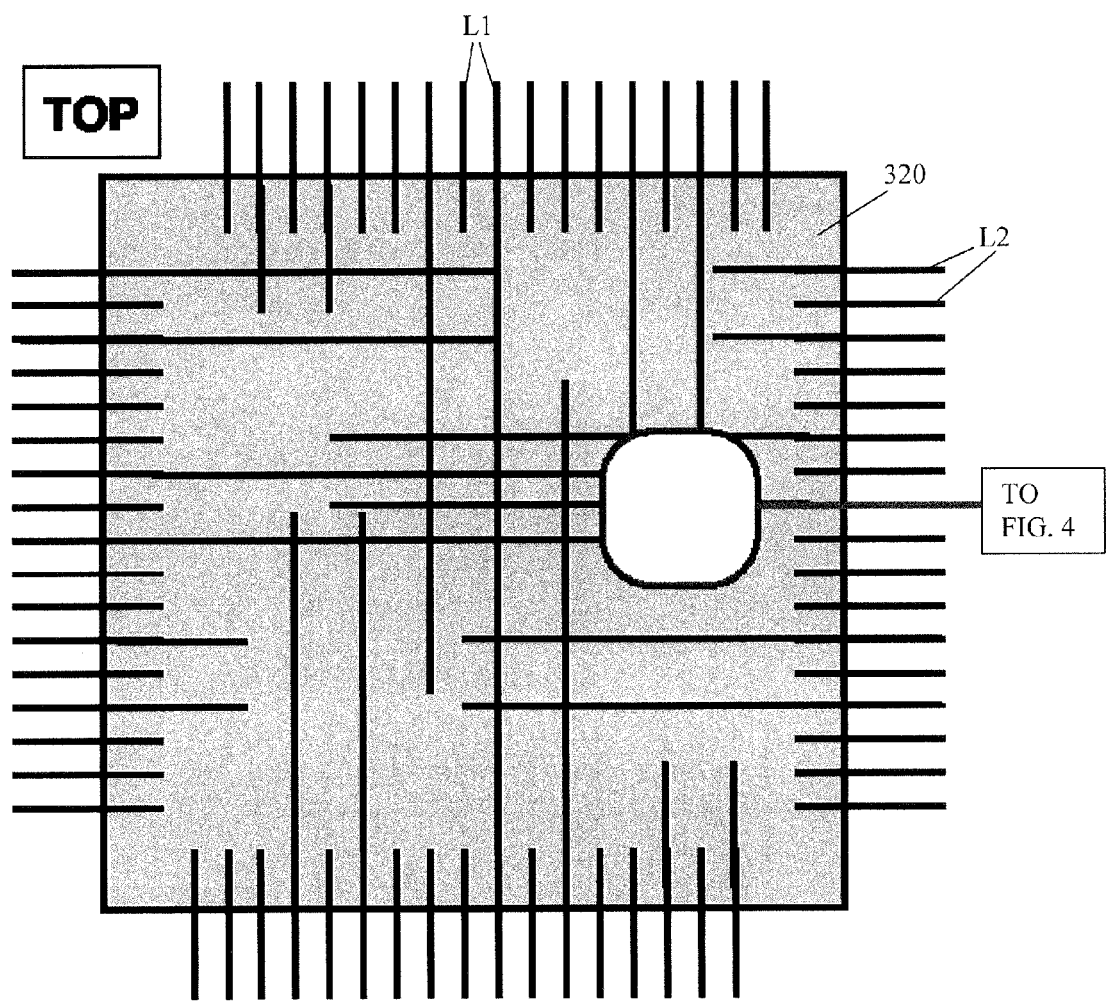
FIG. 3 is a diagram of a top view of an IC, in accordance with some exemplary embodiments of the disclosed subject matter.

Referring to FIG. 3, a top view of an exemplary IC is illustrated. The IC 320 can have wires in multiple layers, for example a first layer L1 and a second layer L2. The IC can have any number of layers suitable for the purpose of the IC.

Figure 4:
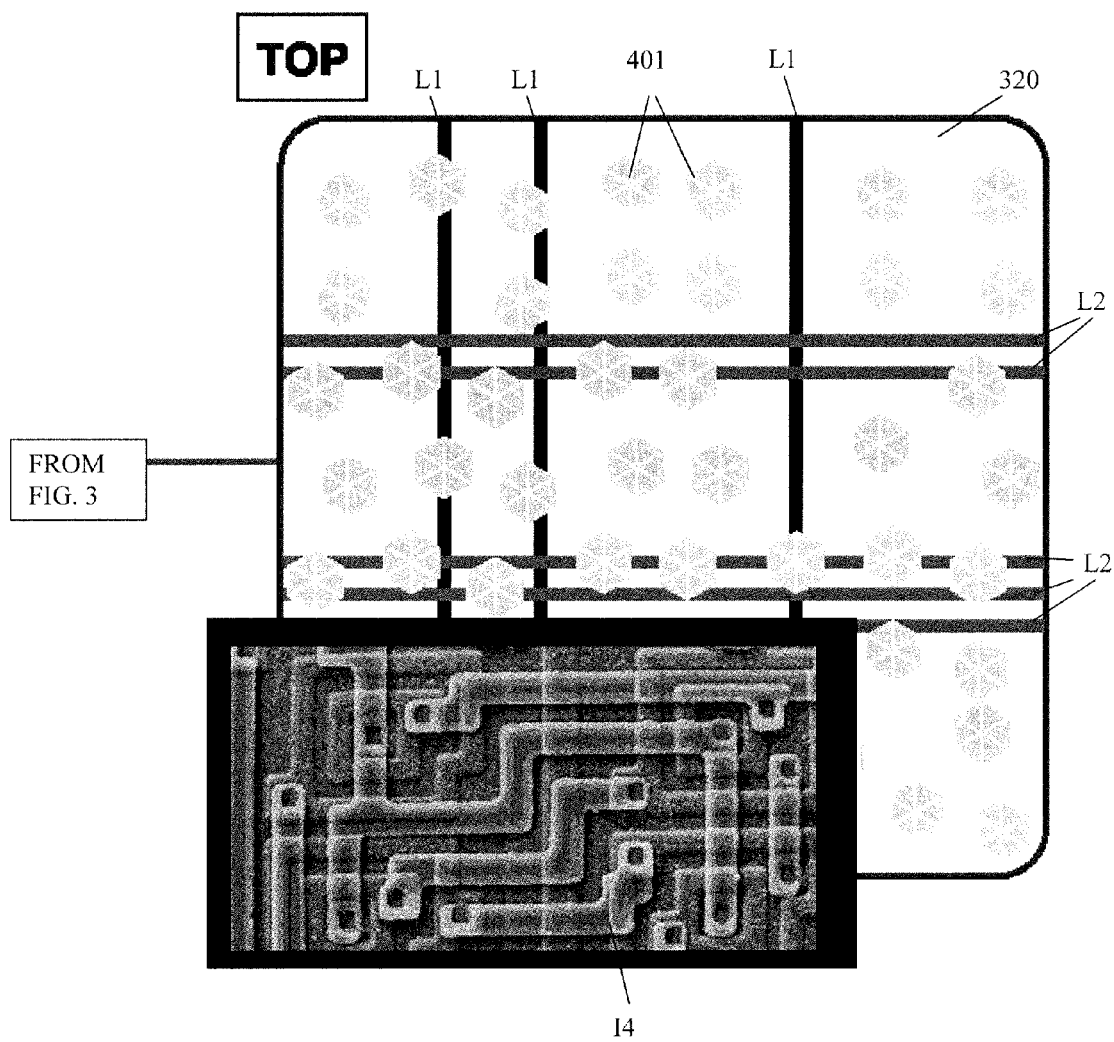
FIG. 4 is a diagram of a top view of nanodiamonds covering the surface of an IC, in accordance with some exemplary embodiments of the disclosed subject matter.

Referring to FIG. 4, a top view of exemplary nanodiamonds covering a portion of the surface of the IC 320 is illustrated. As in FIG. 3, the IC 320 can have wires in multiple layers, for example a first layer L1 and a second layer L2. The IC can have any number of layers suitable for the purpose of the IC. Nanodiamonds 401, each with at least one NV color center (not pictured), can be positioned on the surface of the IC 320, as further discussed below. The inset I4 shows an image of the surface of an IC with overlapping wires from multiple lasers obtained using a TEM.

Figure 5:
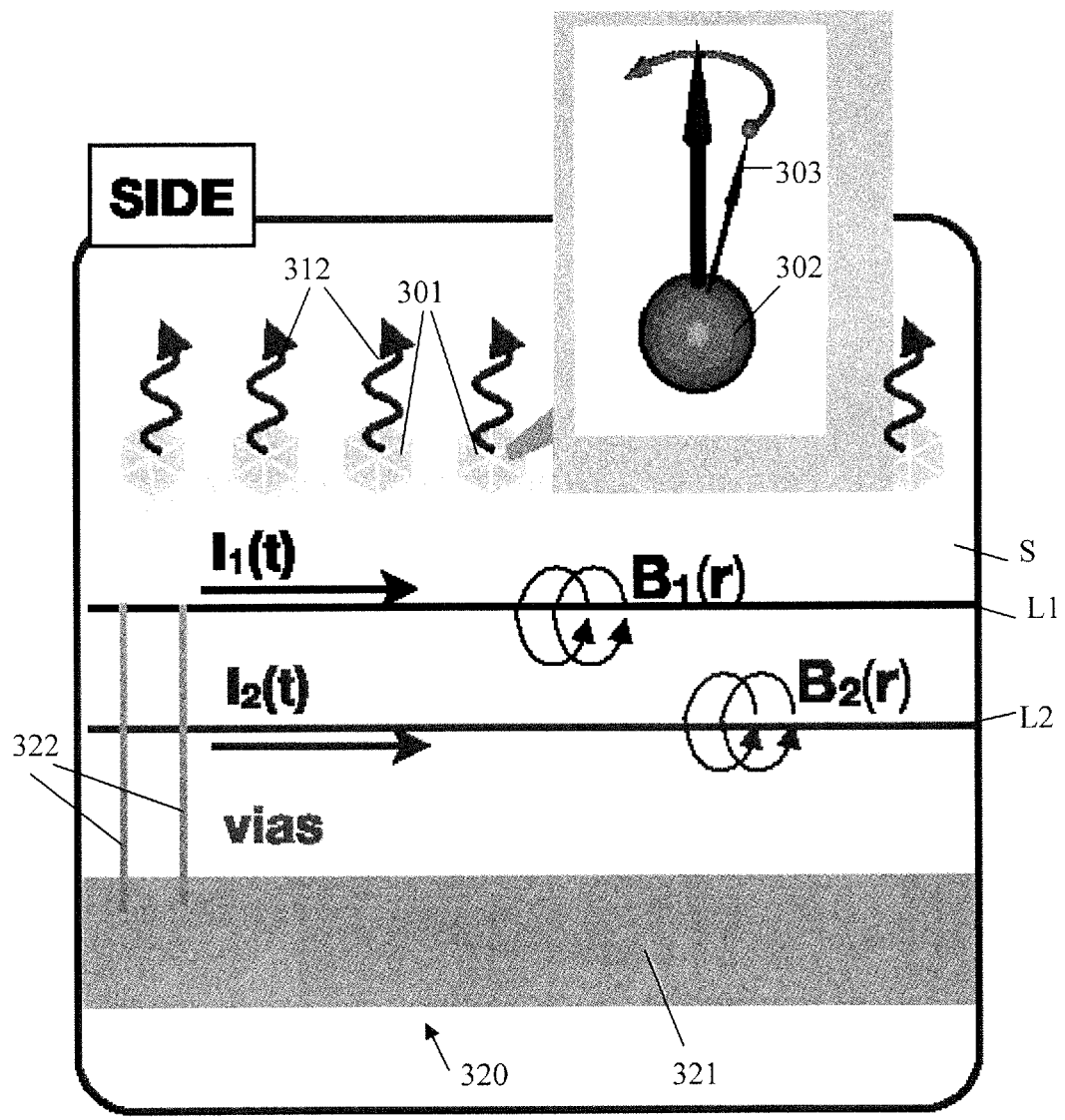
FIG. 5 is a diagram of a side view of nanodiamonds covering the surface of an IC, in accordance with some exemplary embodiments of the disclosed subject matter.

Referring to FIG. 5, a side view of exemplary nanodiamonds covering a portion of the surface of the IC 320 is illustrated. As in FIGS. 3 and 4, the IC 320 can have wires in multiple layers, for example a first layer L1 and a second layer L2. The IC can have any number of layers suitable for the purpose of the IC. Nanodiamonds 301, each with at least one NV color center 302 (shown in the inset), can be positioned on the surface of the IC 320, as further discussed below. A wire in the first layer L1 can have a current $I_1(t)$ and a corresponding magnetic field $B_1(r)$. Similarly, a wire in the second layer L2 can have a current $I_2(t)$ and a corresponding magnetic field $B_2(r)$. The IC 320 can also have vias 322 extending between the layers. The IC can further have a base layer 321, for example a silicon layer. There can be a spacer S between the layers L1 and L2 and the nanodiamonds 301. The NV centers 302 of nanodiamonds 301 can emit photons 312 when excited using optical and microwave excitation, as discussed above and below. The spin state of the NV centers 302 can respond to the magnetic fields $B_1(r)$ and $B_2(r)$ created by the currents $I_1(t)$ and $I_2(t)$, as indicated by the arrows 303.

FIG. 6 is shows a flowchart of an exemplary method for detecting a characteristic of an integrated circuit. Referring also to FIG. 5 as an example for convenience, at least one diamond structure 301 can be deposited onto a side of an integrated circuit 320 (601). For example, the diamond structure 301 can be a nanodiamond, and at least one nanodiamond 301 can be deposited onto the top surface of the integrated circuit 320 (601). For example, the nanodiamonds can be deposited by drop-casting, spin-coating, or atomizing. Each nanodiamond 301 can have at least one color center 302 therein. For example, the color center 302 can be an NV center. An electromagnetic pump field (not pictured) can be applied to the NV center 302 of the nanodiamond 301 (602). For example, the nanodiamonds 301 can be continuously pumped with green laser at approximately 532 nm with a power near 1 mW focused to a 500 nm spot. For pulsed excitation, the power can scale down with the duty cycle. In some embodiments, optical pumping can occur at discrete times. For example, a first pulse of pump light can be applied to drive the NV spin states into the $m_s=0$ sublevel. An additional pulse of pump light can be applied for readout.

The spin state of each NV center 302 can be monitored by measuring an emission of photons 312 from the NV center 302 resulting from the electromagnetic pump field (not pictured) and an electromagnetic radiation of the integrated circuit 320 (603). Certain magnetometry techniques can require the use of an external microwave pulse to excite the NV center 302 in order to monitor its spin state. In accordance with some embodiments of the disclosed subject matter, an external microwave pulse can be unnecessary because of the magnetic fields generated by the IC 320. For example, in an NV center 302 with a charge state NV-, zero field splitting $D_{ZFS}$ can be about 2.87 GHz while the NV- center is pumped with a steady green laser, which can pump the spin population into $m_s=0$. When the frequency of the IC 320 becomes resonant with the $D_{ZFS}$, the $m_s=0$ and $m_s=+1,-1$ levels can be coupled, which can cause the spin population to transfer to the $m_s=+1,-1$ levels, which on average can have lower fluorescence than the $m_s=0$ spin level. Note that the NV- zero field splitting of 2.87 GHz can be very close to the clock frequency of certain commercially available ICs.

The characteristic of interest of the IC 320, e.g. local currents in the IC 320 or local temperatures in the IC 320, can be detected based on a correlation between the emission of photons 312 and the characteristic (604), as further discussed below. For example, the fluorescence brightness of an exemplary NV- center 302 can respond to the magnetic field created by currents in the IC 320.

By way of example and not limitation, alternating current (AC) in IC 320 gives rise to a time-varying magnetic field, such as $B_1(r)$ or $B_2(r)$, which can then be detected using, e.g., a spin-echo based spin sequence such as Rabi sequence or other suitable echo sequence. After a spin sequence is applied using optical pumping (602) and microwave fields from the IC 320, the NV- spin state can be read out through the brightness of the fluorescent response 312. Thus, optical intensity from the NV- ultimately can indicate the magnetic field strength at the location of the NV-. The technique can be sensitive, enabling the detection of magnetic fields on the nT/sqrt(Hz) scale, which can be sufficient to detect the magnetic field associated with a single electron at 10 nm distance. For example, currents within the IC 320 can be modulated at a convenient frequency, such as ~1 MHz, which can correspond to the inverse of the electron spin phase coherence ($T_2$) time of NV centers 302 in nanodiamonds 301. The current in the IC 320 can be modulated with small contrast, e.g., a small amplitude modulation can exist on all currents within the IC 320. The amplitude can chosen to be small enough (e.g., 1-10% of the mean current under normal operation) so that the chip functions normally. Because this technique can require fast optical readout of NV fluorescence 312, e.g., on the order of hundreds of kHz, a similarly fast detector or detector array (e.g., in a camera) can be used.

By way of example and not limitation, the technique of the preceding paragraph can be modified by sweeping the lock-in frequency of the detection without applying an amplitude modulation to the IC currents. In this example, the NV can be in a stationary magnetic field, which can be zero or up to several hundred Gauss. The transition frequencies between $m_s=0$ and $m_s=+1, -1$ levels at particular frequencies $\omega_{-1}, \omega_{+1}$, which can be in the range of 2-3 GHz. If the NV is continuously pumped by green pump light, it can be initialized primarily in the $m_s=0$ state. If an electromagnetic field emanating from the currents in the integrated circuit are resonant with magnetic sublevel transitions near $\omega_{-1}, \omega_{+1}$, then the NV magnetic sublevel population can be moved to the $m_s=+1, -1$ levels, which can be associated with lower photoluminescence. Using this optically detected magnetic resonance, electromagnetic fields can be detected with frequencies at $\omega_{-1}, \omega_{+1}$. The current in an integrated circuit can have a periodicity determined by the clock of the integrated circuit. This clock can be tuned so that the integrated circuit runs at a frequency near $\omega_{-1}, \omega_{+1}$. By tuning the clock frequency across near $\omega_{-1}, \omega_{+1}$, a spectrum of the currents within the chip can be measured via the spin-dependent fluorescence of the NV centers.

By way of example and not limitation, the clock frequency of the IC 320 can be modulated across the NV– zero field splitting $D_{ZFS}$, which can be about 2.87 GHz, while the NV– is pumped with a steady green laser, which pumps the spin population into $m_s=0$. When the frequency of the IC 320 becomes resonant with the $D_{ZFS}$, the $m^s=0$ and $m_s=+1,-1$ levels can be coupled, which can cause the spin population to transfer to the $m_s=+1,-1$ levels, which on average can have lower fluorescence. The spectral components of the current of the IC 320 can have a peak at the clock frequency. The stronger the magnitude of the microwave field generated by the IC 320, the lower the brightness of the NV-fluorescence, when the NV is in an un-saturated driving regime. Thus, the magnetic field, i.e. microwave field, due to currents in the IC 320 can be detected by a brightness change of the NV– fluorescence 312 of the nanodiamonds 301, which can be detected using a suitable camera (e.g., a cooled CCD or emCCD camera). Note the fortuitous coincidence that the NV– zero field splitting of 2.87 GHz can be close to the clock frequency of some ICs.

By way of example and not limitation, as a variation to example in the preceding paragraph, ensembles of NV centers in bulk or diamond nanocrystals can be used. These ensembles of NV centers can be oriented at different angles with respect to one another so that they experience different Zeeman splitting under the application of an external magnetic field, as further discussed below. For example, the Zeeman splitting can be large so that NV $m_s=0$ to $m_s=\pm 1$ transitions can occur for frequencies from direct current (DC), i.e. 0 Hz, to above 5 GHz. The magnetic (i.e. microwave) field produced by currents within the IC 320 can have a power spectrum that depends on the information (and coding) of currents within the wires of the IC 320. This power spectrum can then be observed in electron spin resonance (ESR) dips of the fluorescence 312 of the nanodiamonds 301, as described above. This technique can enable field measurements at high frequency (e.g., greater than 100 MHz).

By way of example and not limitation, a relatively weak DC magnetic field can be applied across the NV centers 302, e.g., using a permanent magnet (not pictured), to shift the magnetic sublevels of the NV center by Zeeman effect. For example, the AC magnetic field of the IC 320 can drive the NV center 302 into the $m_s=+1$ state, which can result in lower resulting fluorescent intensity due to transition through the shelving state. The current in the IC 320 can be detected by monitoring the spin state by measuring the intensity of the fluorescent response 312.

By way of example and not limitation, a resonant AC magnetic field can be applied across the NV centers 302, e.g. using a microwave antenna (not pictured), concurrently with the AC magnetic field applied by the IC 320. The resulting AC magnetic field driving the NV centers 302 is the sum of the external AC field and the field from the IC 320, which can depend on the relative phase between the AC fields. The phase of the current in the IC 320 can be detected by monitoring the spin state by measuring the intensity of the fluorescent response 312.

By way of example and not limitation, in certain cases, it can be useful to image not just the top layer L1, but to image currents in lower layers, e.g. L2, of the IC 320. For example. some IC chips can have more than 20 interconnect layers, in which the lowest-lying layers can have wires that can be below 100 nm in diameter. Imaging currents in multiple layers of IC 320 can be accomplished by reconstruction of the measured magnetic field at the surface. For example, it can be useful to measure the full vector nature of the magnetic field. The magnetic field sensing techniques described above can accomplish vector field imaging because the brightness drop of the fluorescent response 312 of any given NV– center 302 can depend on the inner product of the magnetic dipole of the NV center 302 with the magnetic field from the IC 320. The internal dipole of a given NV center 302 can be determined and calibrated through an external microwave or magnetic field, as discussed below.

By way of example and not limitation, temperature can be detected by a known shift in the ground state zero field splitting $D_{ZFS}$ of the NV– system at a rate of $dD_{ZFS}/dT=-74$ kHz/K. The NV– zero field splitting resonance can have a line width below 50 MHz. Using shot-noise limited detection, the line width can be estimated to 50 MHz/sqrt(n*t), where n*t equals the number of photons detected. Assuming a photon flux n of about 100 kHz, we therefore assume that about 3 Kelvin of temperature change is detectable after about 1 second of averaging. The temperature change can be observed simultaneously with magnetic field imaging, noting that the small shift in the $D_{ZFS}$ even for a relatively large temperature shift of 100K would cause only a negligible change in the fluorescence amplitude.

By way of example and not limitation, the spatial resolution of the magnetic field detection can be governed by the ability to locate NV– centers under the microscope, photodetector, or other monitoring device. Typically, this spatial resolution can on the order of the diffraction limited spot size, which can be several hundreds of nanometers for a high-numerical aperture (NA) objective. However, super-resolution microscopy techniques, such as "Deterministic Emitter Switch Microscopy" (DESM) or "Stimulated Emission Depletion" (STED), can be employed to resolve NV-emitters to below 10 nm. In particular, DESM can enable this resolution in wide-field microscopy. Thus, a wide region of the IC 320 can be imaged with relatively high optical resolution.

Figure 7:
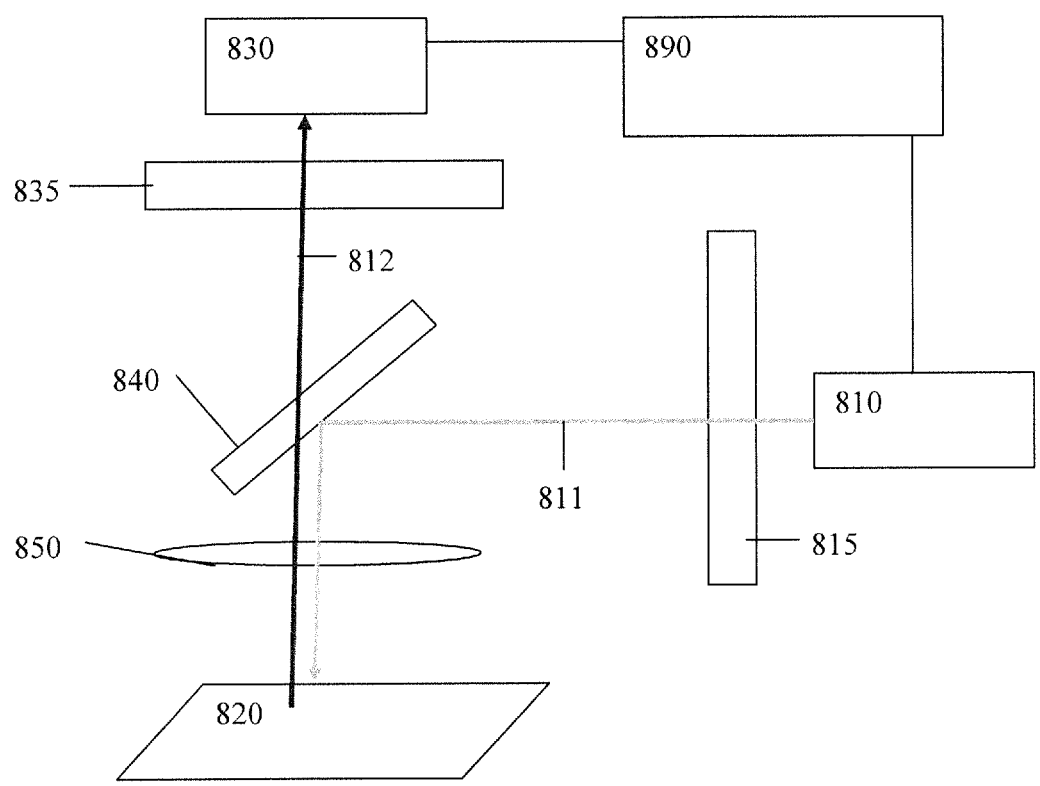
FIG. 7 is a schematic diagram of a system for imaging a characteristic of an IC, in accordance with some exemplary embodiments of the disclosed subject matter.

By way of example and not limitation, referring also to FIG. 7, an exemplary system for imaging a characteristic of an IC is illustrated. However, various modifications will become apparent to those skilled in the art from the following description and the accompanying figures. Such modifications are intended to fall within the scope of the appended claims.

By way of example and not limitation, a confocal scanning technique or emCCD camera technique can be employed. Any suitable emCCD can be employed, for example the ProEM available from Princeton Instruments. In general, a two-dimensional scan of a IC with m NV centers can be given by:

$$I(x,y,\omega) = \Sigma_i{}^m I_i \alpha_i [1 - D_i(P_{RF}, P_{pump}, \omega) N_i(x,y)], \quad (1)$$

where I is intensity, $\alpha$ is collection efficiency; $D_i$ is electron spin resonance dips; $P_{RF}$ is power of the radio-frequency field; $P_{pump}$ is the power of the optical 532 nm pump field; $\omega$ is the crystal field splitting frequency, and N is a two-dimensional Gaussian distribution with general defining parameters. A confocal scan taken off resonance can be subtracted from a confocal scan taken on resonance to isolate only the photons emitted from the NV centers with frequencies $\omega_i$, given by:

$$I(x,y,\omega_O) - I(x,y,\omega_i) = I_i \alpha_i C_i(P_{RF}, P_{pump}) N_i(x,y) \quad (2)$$

$D_i$ can be given by:

$$Di(P_{RF}, P_{pump}, \omega) = \frac{C_i(\gamma_i/2)^2}{(\gamma_i/2)^2 + (\omega - \omega_i)^2}, \quad (3)$$

where $C_i(P_{RF}, P_{pump})$, $\gamma_i(P_{RF}, P_{pump})$, and $\omega_i = \omega_O \pm \vec{B} \cdot \vec{\mu}_i$. $N_i(x,y)$ can be given by:

$$N_i(x,y) = \frac{e^{\frac{-1}{2(1-\rho_i^2)} \left[ \frac{(x-\mu_{ix})^2}{\sigma_{ix}^2} + \frac{(x-\mu_{iy})^2}{\sigma_{iy}^2} - \frac{2\rho_i(x-\mu_{ix})(x-\mu_{iy})}{\sigma_{ix}\sigma_{iy}} \right]}}{2\pi\sigma_{ix}\sigma_{iy}\sqrt{1-\rho_i^2}}. \quad (4)$$

The precision with which the two-dimensional position of the NV center can be known can increase with the square root of the integration time due to the poissonian nature of the source. Such precision can be limited by the environment, including piezoelectric drift of an IC holder and thermal fluctuations throughout the setup.

The Zeeman splitting of an NV center can be measured by using optically detected magnetic resonance (ODMR). For example, a continuous wave of green pump laser can be applied for polarizing the spin of the NV into the $m_s=0$ ground state, and an electromagnetic field in the GHz regime generated by the IC can resonantly excite the NV from the $m_s=0$ ground state to the $m_s=\pm1$ ground states. Due to the bias of the $m_s=\pm1$ excited states to decay into a metastable singled state with a longer life (e.g., 300 ns) than the lifetime of the $m_s=0$ excited state (e.g., 10 ns), the fluorescence into the 637-800 nm band can decrease.

A plurality of diamond nanoparticles, or nanodiamonds, (not pictured) can be deposited onto the surface of IC 820 (601). One or more of the nanodiamonds can have an NV center therein. An electromagnetic pump field can be applied to the nanodiamonds (602). For example, the nanodiamonds can be optically pumped (602) to excite the NV centers contained therein. For example, the nanodiamonds can be continuously pumped with green laser at approximately 532 nm with a power near 1 mW focused to a 500 nm spot. For pulsed excitation, the power can scale down with the duty cycle. In some embodiments, optical pumping can occur at discrete times. For example, a first pulse of pump light can be applied to drive the NV spin states into the $m_s=0$ sublevel. An additional pulse of pump light can be applied for readout.

Optical pumping (602) can be accomplished with a suitable light source 810, which can include a green laser capable of emitting light at 532 nm. Addition optics 815 and 835 can be employed to guide, filter, focus, reflect, refract, or otherwise manipulate the light. Such optics can include, for example, a pinhole aperture and/or barrier filter (not shown). Additionally, a dichromatic mirror 840 can be used to direct pump light to the IC 820 while transmitting a fluorescent response. For example, the light source 810 can be arranged such that pump light 811 is reflected off of a dichromatic mirror 840 and towards the IC 820. A fluorescent response from the IC 820 will be directed through the dichromatic mirror 840 in a direction orthogonal to the orientation of the light source 810.

The pump light 811 can be directed through an objective 850 to the IC 820. Photons in the pump light 811 can be absorbed by the NV centers within the nanodiamonds exposed to the IC 820, thereby exciting the NV center into an excited state. The NV can then transition back to the ground state, emitting fluorescent response 812, e.g., a photon with a wavelength between 637 and 800 nm. This fluorescent response can pass through the objective 850 and the dichromatic mirror 840 to a monitoring device 830. For example, the monitoring device 830 can be a photodetector. In certain embodiments, the photodetector 830 can include a photomultiplier. The photodetector 830 can be, for example, an emCCD camera. Alternatively, the photodetector 830 can be a scanning confocal microscope or other suitable photon detector.

In certain embodiments, the axis of the nitrogen vacancy centers in the diamond nanoparticle of the nanodiamond can be aligned at random angles with the magnetic field of the IC 820. The magnetic field of the IC 820 can impart on the NV− electronic ground states a Zeeman splitting between the $m_s=+1$ and a $m_s=+1$ spin sublevels. The value of the Zeeman splitting can depend on the precise alignment between the NV− center, and this alignment can be random, allowing for many different values.

The area of the IC 820 can be divided into a number of pixels, each pixel corresponding to subset of the area. For each pixel, the fluorescent response 812 can be measured corresponding to the frequency of the electromagnetic radiation generated by the currents in the IC 820. In this manner, the location of a single NV center can be addressed due to the particular Zeeman splitting resulting from the precise alignment the magnetic field from the IC and the NV center. For example, an AC magnetic field can be generated by the IC 820 at a the frequency $\omega$ of the IC's clock. A relatively weak DC magnetic field can be applied across the NV centers, e.g., using a permanent magnet (not pictured), to shift the magnetic sublevels of the NV center by Zeeman effect, as discussed above. The AC magnetic field can drive the NV center into the $m_s=+1$ state, which can result in lower resulting fluorescent intensity due to transition through the shelving state. The photodetector 830 can then monitor (603) the spin state by measuring the intensity of the fluorescent response.

By way of example and not limitation, the internal dipole of a given NV center 302 can be determined and calibrated through an external microwave or magnetic field. For example, the area of the IC 820 can be divided into a number of pixels, each pixel corresponding to subset of the area. For each pixel, the fluorescent response 812 can be measured for various microwave pulses. In this manner, the location of a single NV center can be addressed due to the particular Zeeman splitting resulting from the precise alignment between the magnetic nanoparticle and the NV center. For example, a first microwave pulse can be applied at a first frequency $\omega_{+1}$. This first frequency can be tuned to the field splitting frequency of a single NV center based on its Zeeman splitting. This microwave pulse can drive the single NV center into the $m_s=+1$ state, which can result in lower resulting fluorescent intensity due to transition through the shelving state. However, this pulse will not drive any surrounding NV centers into the $m_s=+1$ state because different orientations of the their corresponding magnetic nanoparticles will result in different Zeeman splitting. The photodetector 830 can then measure the intensity of the fluorescent response.

A second microwave pulse can be applied at a second frequency $\omega_0$. The second frequency can be tuned to the zero-field splitting frequency of a single NV center, e.g., 2.87 GHz. The photodetector 830 can then measure the intensity of the fluorescent response. In like fashion, at least a third microwave pulse can be applied at a third frequency $\omega_{-1}$. The third frequency can be tuned to the field splitting frequency of a single NV center based on its Zeeman splitting. This microwave pulse can drive the single NV center into the $m_s=-1$ state, which can result in lower resulting fluorescent intensity due to transition through the shelving state. The photodetector 830 can then measure the intensity of the fluorescent response.

The location of the single NV center can then be determined based on the intensities of the fluorescent responses corresponding to the first, second, and third microwave pulses. For example, the control unit 890, which can include a processor and a memory, can subtract the intensities corresponding to frequencies $\omega_{+1}$ and $\omega_{-1}$ from the intensity corresponding to $\omega_0$. Additional processing techniques can be employed to further reduce uncertainty regarding the position of the NV center. Additional processing techniques can be employed to further reduce uncertainty regarding the position of the NV center. For example, to compensate for sample drift, e.g. the IC 820 moving, each acquired image can first be shifted slightly to minimize global offsets from the previous images, which can enable a reduction of susceptibility to sample drift. Each pixel can then be combined and displayed, thereby providing a graphical representation or image of the location of one or more NV centers. The techniques disclosed herein can be repeated for a plurality of NV centers, which can allow for tracking of individual NV centers.

The characteristic of interest, e.g. current in the IC 820, can then be detected (604) based on the intensities of the fluorescent responses and the correlation between the fluorescent response and the characteristic. For example, the control unit 890, which can include a processor and a memory, can calculate the current based on the brightness drop of the NV− centers.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

What is claimed is:

1. A method for detecting a characteristic of an integrated circuit, comprising:
   depositing at least one diamond structure, having at least one color center therein, onto a side of the integrated circuit;
   applying an electromagnetic pump field to the at least one diamond structure;
   monitoring a spin state of the at least one color center by measuring an emission of photons from the at least one color center resulting from the electromagnetic pump field and an electromagnetic radiation of the integrated circuit; and
   detecting the characteristic of the integrated circuit based on a correlation between the emission of photons and the characteristic.

2. The method of claim 1, further comprising applying a direct current magnetic field to the at least one color center.

3. The method of claim 1, wherein the characteristic comprises one of a current or a temperature.

4. The method of claim 1, wherein the color center comprises a nitrogen vacancy (NV) center, the monitoring comprising monitoring a positive spin state of the NV center, a ground spin state of the NV center, and a negative spin state of the NV center.

5. The method of claim 1, wherein the characteristic comprises a current, the method further comprising modulating the current at a frequency corresponding to an inverse of an electron spin phase coherence time of the color center.

6. The method of claim 1, wherein the characteristic comprises a current, the method further comprising:
   applying a direct current magnetic field to the at least one color center; and
   sweeping the direct current magnetic field to shift a magnetic sublevel of the at least one color center by Zeeman effect.

7. The method of claim 1, wherein the characteristic comprises a current, the method further comprising modulating a clock frequency of the integrated circuit.

8. The method of claim 1, further comprising calibrating an internal dipole of the color center.

9. The method of claim 8, the detecting comprising determining a full vector nature of a magnetic field resulting from the characteristic based on a predetermined correlation between the emission of photons, the internal dipole, and the magnetic field; and
   detecting the characteristic for each layer of a plurality of layers within the integrated circuit based on a predetermined correlation between the magnetic field and the characteristic.

10. The method of claim 1, wherein the at least one diamond structure comprises a plurality of nanodiamonds, the depositing comprising:
    solubilizing the nanodiamonds in a solvent; and
    depositing the nanodiamonds onto a side of the integrated circuit by one of drop-casting, spin-coating, or atomizing.

11. A system for detecting a characteristic of an integrated circuit, comprising:
    a receptacle adapted to receive the integrated circuit;

at least one diamond structure, having at least one color center therein, disposed on a side of the integrated circuit;

an electromagnetic pump field source adapted to apply an electromagnetic pump field to the at least one diamond structure;

a monitoring device, coupled to the receptacle and adapted to monitor a spin state of the at least one color center by measuring an emission of photons from the at least one color center resulting from the electromagnetic pump field and an electromagnetic radiation of the integrated circuit to thereby detect the characteristic of the integrated circuit based on a predetermined correlation between the emission of photons and the characteristic.

12. The system of claim 11, further comprising a direct current magnetic field source, coupled to the receptacle and adapted to apply a direct current magnetic field to the at least one color center.

13. The system of claim 11, further comprising an alternating current magnetic field source, coupled to the receptacle and adapted to apply an alternating current magnetic field to the at least one color center.

14. The system of claim 11, wherein the diamond structure comprises one of a nanodiamond or a bulk diamond crystal.

15. The system of claim 11, wherein the characteristic comprises one of a current or a temperature.

16. The system of claim 11, wherein the color center comprises a nitrogen vacancy (NV) center, and wherein the monitoring device is adapted to monitor an $m_s=+1$ spin state of the NV center, an $m_s=0$ spin state of the NV center, and the $m_s=-1$ spin state of the NV center.

17. The system of claim 11, wherein the characteristic comprises a current modulated at a frequency between an inverse of an electron spin phase coherence time of the color center and 10 MHz.

18. The system of claim 12, wherein the characteristic comprises a current, the direct current magnetic field source adapted to sweep the direct current magnetic field to shift a magnetic sublevel of the at least one color center by Zeeman effect.

19. The system of claim 11, wherein the characteristic comprises a current, and wherein the integrated circuit has a modulated clock frequency.

20. The system of claim 13, wherein the characteristic comprises a current, the alternating current magnetic field adapted to interfere with the electromagnetic radiation of the integrated circuit.

21. The system of claim 11, the color center including a calibrated internal dipole, and wherein the monitoring device is adapted to detect the characteristic for each layer of a plurality of layers within the integrated circuit based on a predetermined correlation between the emission of photons, the internal dipole, the magnetic field, and the characteristic.

* * * * *